(12) United States Patent
Kruglick

(10) Patent No.: US 8,855,751 B2
(45) Date of Patent: Oct. 7, 2014

(54) MULTIDIRECTIONAL SCAN AND ALGORITHMIC SKIN HEALTH ANALYSIS

(75) Inventor: Ezekiel Kruglick, Poway, CA (US)

(73) Assignee: Empire Technology Development LLC, Wilmington, DE (US)

( * ) Notice: Subject to any disclaimer, the term of this patent is extended or adjusted under 35 U.S.C. 154(b) by 678 days.

(21) Appl. No.: 12/714,011

(22) Filed: Feb. 26, 2010

(65) Prior Publication Data

US 2011/0213253 A1 Sep. 1, 2011

(51) Int. Cl.
*A61B 5/00* (2006.01)

(52) U.S. Cl.
CPC .............. *A61B 5/0064* (2013.01); *A61B 5/444* (2013.01)
USPC ........... 600/477; 600/476; 600/478; 600/479; 600/480

(58) Field of Classification Search
USPC .......................................... 600/407, 476, 477
See application file for complete search history.

(56) References Cited

U.S. PATENT DOCUMENTS

| | | | |
|---|---|---|---|
| 4,031,743 A | 6/1977 | Kossoff et al. | |
| 2004/0015082 A1 | 1/2004 | Vernet | |
| 2005/0228280 A1 | 10/2005 | Ustuner et al. | |
| 2006/0227137 A1 | 10/2006 | Weyrich et al. | |
| 2006/0239547 A1* | 10/2006 | Robinson et al. | 382/162 |
| 2007/0020623 A1* | 1/2007 | Petersohn et al. | 435/6 |
| 2007/0049832 A1* | 3/2007 | Edgar et al. | 600/476 |
| 2007/0232962 A1 | 10/2007 | Zumeris et al. | |
| 2008/0139900 A1 | 6/2008 | Randlov et al. | |
| 2008/0200777 A1 | 8/2008 | Issachar et al. | |
| 2009/0174878 A1 | 7/2009 | Wadman | |

FOREIGN PATENT DOCUMENTS

| | | |
|---|---|---|
| EP | 1795131 A1 | 6/2007 |
| SG | 2009145735 A1 | 12/2009 |
| SU | 1833817 A1 | 10/1990 |
| WO | 2009115947 A1 | 9/2009 |
| WO | 2011106035 | 9/2011 |

OTHER PUBLICATIONS

ISR and Written Opinion, PCT/US2010/046694.
Curiel-Lewandrowski, C., et al., "Use of In Vivo Confocal Microscopy in Malignant Melanoma an Aid in Diagnosis and Assessment of Surgical and Nonsurgical Therapeutic Approaches," Am Med Assoc, vol. 140, Issue 9, pp. 1127-1132.
González, S, and Gilaberte-Calzadal‡, Y., "In vivo reflectance-mode confocal microscopy in clinical dermatology and cosmetology," International Journal of Cosmetic Science, vol. 30, No. 1 (2008): 1-17.
D'Eon, Advanced Techniques for Realistic Real-Time Skin Rendering; Chapter 14 from book GPU Gems 3; 58 pages.
Tsumura, Image-based skin color and texture analysis/synthesis by extracting hemoglobin and melanin information in the skin; Article; 10 pages.

(Continued)

*Primary Examiner* — Tse Chen
*Assistant Examiner* — Mark Remaly
(74) *Attorney, Agent, or Firm* — Jensen & Puntigam, PS

(57) ABSTRACT

Technologies generally applicable to detecting skin conditions are disclosed. A computer graphics scanning apparatus may be configured to capture skin image data, and use the captured skin image data to calculate a subsurface transfer function for the skin, which may identify subsurface properties of the skin. The identified subsurface properties may be correlated to one or more skin conditions for medical and/or cosmetic treatment diagnosis.

26 Claims, 6 Drawing Sheets

(56) References Cited

OTHER PUBLICATIONS

U.S. Appl. No. 12/714,060; Echogram Detection of Skin Conditions; filed Feb. 26, 2010.

Donner, C., et al., "A Layered, Heterogeneous Reflectance Model for Acquiring and Rendering Human Skin," ACM Transactions on Graphics, Dec. 2008, vol. 27, No. 5, pp. 1-12.

Miller, K.E., "Early Detection of Metastatic Melanoma Using Ultrasound," American Family Physician, Dec. 1, 2000, vol. 62, No. 11, pp. 2522.

Wagner, R.F., et al., "Residents' Corner: Diagnoses of Skin Disease: Dermatologists vs. Nondermatologists (abstract)," The Journal of Dermatologic Surgery and Oncology, 1985, vol. 11, No. 5, pp. 476-479.

Notice of Allowance, U.S. Appl. No. 12/714,060, Jul. 16, 2013.

Lucid, Inc., "New Studies Show Effectiveness of Reflective Confocal Microscopy," PRLog Global Press Release Distribution, accessed at http://www.prlog.org/10026545-new-studies-show-effectiveness-of-reflective-confocal-microscopy.html, Aug. 7, 2007, pp. 2.

Rochester., "New Studies Show Effectiveness of Reflective Confocal Microscopy," accessed at http://www.prlog. org/10026545-new-studies-show-effectiveness-of-reflective-confocal-microscopy.html, Aug. 7, 2007, pp. 2.

Agero, A.L.C., et al., "Reflectance confocal microscopy of pigmented basal cell carcinoma," Journal of the American Academy of Dermatology 54, No. 4 (2006): pp. 638-643.

Barnard, C.M, and Goldyne, M.E., "Evaluation of an asynchronous teleconsultation system for diagnosis of skin cancer and other skin diseases," Telemedicine Journal and e-Health 6, No. 4 (2000): 379-384.

Cassileth BR., et al., "How well do physicians recognize melanoma and other problem lesions?," Journal of the American Academy of Dermatology, 1986;14, pp. 555-560.

Claridge, E, and Preece, SJ., "An inverse method for the recovery of tissue parameters from colour images," In Information Processing in Medical Imaging, (2003), 306-317.

Cotton, S.D., and Claridge, E., "Developing a predictive model of human skin colouring," In Proceedings of SPIE Medical Imaging, (1996), 814-825.

Craig, D., et al., "A Layered, Heterogeneous Reflectance Model for Acquiring and Rendering Human Skin," ACM Trans. Graph. 27, No. 5 (2008): pp. 1-12.

Curiel-Lewandrowski, C., et al., "Use of in Vivo Confocal Microscopy in Malignant Melanoma An Aid in Diagnosis and Assessment of Surgical and Nonsurgical Therapeutic Approaches," Am Med Assoc, vol. 140, Issue 9, pp. 1127-1132, (published 2004).

Donner, C., and Jensen, H. W. 2005. "Light Diffusion in Multi-Layered Translucent Materials," ACM Transactions on Graphics, vol. 24, Issue 3 Jul. 2005, pp. 1032-1039.

Gerbert B., et al., Primary care physicians as gatekeepers in managed care. Arch Dermatol, 1996;132:1030-1038.

Gonzàlez, S, and Gilaberte-Calzada‡, Y., "In vivo reflectance-mode confocal microscopy in clinical dermatology and cosmetology," International Journal of Cosmetic Science, vol. 30, No. 1 (2008): 1-17.

Howard, K.K., et al., "Evaluation of melanoma/skin cancer screening in Massachusetts. Preliminary results," Cancer 65, No. 2 (1990): 375-379.

Jerant, A.F, et al., "Early Detection and Treatment of Skin Cancer," American Family Physician, Jul. 15, 2000, vol. 62, No. 2, pp. 357-368.

Marghoob, A.A., et al., "Instruments and new technologies for the in vivo diagnosis of melanoma," Journal of the American Academy of Dermatology, vol. 49, No. 5 (Nov. 2003), pp. 777-797.

Miles, F, and Meehan, J.W., "Visual discrimination of pigmented skin lesions," Health Psychology: Official Journal of the Division of Health Psychology, American Psychological Association, vol. 14, No. 2, (Mar. 1995), pp. 171-177.

Nickell, S., et al., "Anisotropy of light propagation in human skin," Phys. Med. Biol. vol. 45, pp. 2873-2886 (2005).

Oksala, A., "Echogram in Melanoma of the Choroid," J. Ophthalmol 43, pp. 408-414, (1959).

Ramsay DL, and Fox AB., "The ability of primary care physicians to recognize the common dermatoses," Arch Dermatol, vol. 117, No. 10, 620-622 (1981).

Rochester., "New Studies Show Effectiveness of Reflective Confocal Microscopy," accessed at http://www.prlog.org/10026545-new-studies-show-effectiveness-of-reflective-confocal-microscopy.html, Aug. 7, 2007, pp. 2.

Wolbarsht, M.L., "A proposal to localize an intraocular melanoma by photoacoustic spectroscopy," Soviet Journal of Quantum Electronics, vol. 11, No. 12, pp. 1623-1624 (1981).

Weyrich, Analysis of Human Faces using a Measurement-Based Skin Reflectance Model; Article; 2006; 12 pages.

D'Eon, Advanced Techniques for Realistic Real-Time Skin Rendering; Chapter 14 from book GPU Gems 3; 58 pages, (published 2007).

Pellacani, In vivo asseessment of melanocytic nests in nevi and melanomas by reflectance confocal microscopy; Article, Modern Pathology (2005) 18; 6 pages.

Igarashi, The Appearance of Human Skin; Technical Report CUCS-024-05; Jun. 2005; 88 pages; New York NY, USA.

Thalmann, Virtual Clothes, Hair and Skin for Beautiful Top Models; Article; 1998; 19 pages.

Jensen, A Practical Model for Subsurface Light Transport; Article Aug. 2001; 8 pages; Los Angeles CA, USA.

Tsumura, Image-based skin color and texture analysis/synthesis by extracting hemoglobin and melanin information in the skin; Article; 10 pages, (published 2003).

Yovel, Plant Classification from Bat-Like Echolocation Signals; Article; 2008; vol. 4, Issue 3, PLOS Computational Biology; 13 pages.

U.S. Appl. No. 12/714,060; Multidirectional Scan and Algorithmic Skin Health Analysis; filed Feb. 26, 2010.

* cited by examiner

MULTIDIRECTIONAL SCAN AND ALGORITHMIC SKIN HEALTH ANALYSIS

CROSS-REFERENCE TO RELATED APPLICATIONS

This application is related by subject matter to U.S. patent application Ser. No. 12/714,060, filed Feb. 26, 2010, entitled "ECHOGRAM DETECTION OF SKIN CONDITIONS", which is hereby incorporated by reference.

BACKGROUND

Unless otherwise indicated herein, the materials described in this section are not prior art to the claims in this application and are not admitted to be prior art by inclusion in this section.

Large scale tests performed in 1986 and 1987 demonstrated that it may be feasible to conduct effective large scale visual screening for melanoma and other malignant skin lesions. Howard K. Koh et al., "Evaluation of melanoma/skin cancer screening in Massachusetts: Preliminary results," *Cancer* 65, no. 2 (1990), pages 375-379. Such screening could dramatically reduce costs of care and improve life.

Unfortunately, the cost of routine screening by dermatologists is prohibitive. To this day the majority (about 90%) of health systems pay only for screening by a "gatekeeper", generally a patient's primary care physician. C. M. Barnard and M. E. Goldyne, "Evaluation of an asynchronous teleconsultation system for diagnosis of skin cancer and other skin diseases," *Telemedicine Journal and e-Health* 6, no. 4 (2000), pages 379-384. Non-specialists such as most primary care physicians have only a 50% probability of identifying malignant skin lesions—functionally equivalent to flipping a coin. See, e.g., Ramsay D L, Fox AB, "The ability of primary care physicians to recognize the common dermatoses," *Arch Dermatol* 117, (1981), pages 620-622; and Cassileth B. R., Clark W. H. Jr., Lusk E. J., et al., "How well do physicians recognize melanoma and other problem lesions?" *J. Am. Acad. Dermatol.* 14 (1986), pages 555-560.

The present disclosure identifies and appreciates that conventional approaches of screening for certain skin conditions are limited and inadequate, due to prohibitive costs of doing so effectively, and that improved accuracy screening technologies allowing automated screening and/or screening by non-specialist medical caregivers, for skin features that involve more than cosmetic skin alteration, would be beneficial for better advance detection of skin conditions.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
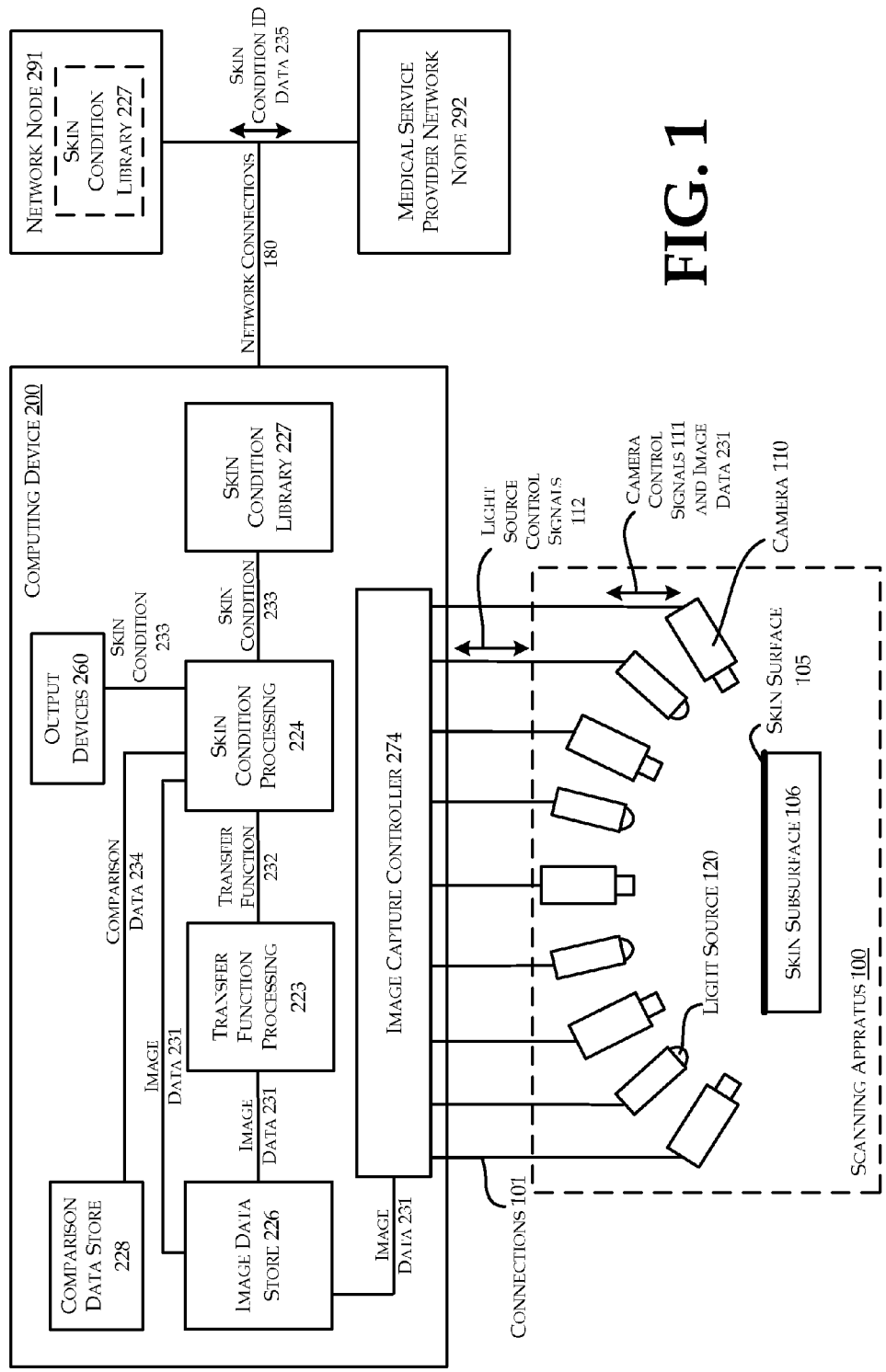
FIG. 1 is a diagram illustrating an example system that may perform a multidirectional scan of a skin surface and perform an algorithmic analysis of collected data to determine presence of a skin condition.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and made part of this disclosure.

The present disclosure is generally drawn, inter alia, to methods, devices, and/or systems related to detecting skin conditions. A computer graphics scanning apparatus may be configured to capture skin image data, and to use the captured skin image data to calculate a subsurface transfer function for the skin, which may identify subsurface properties of the skin. The identified subsurface properties may be correlated to one or more skin conditions for medical and/or cosmetic treatment diagnosis.

FIG. 1 is a diagram illustrating an example system that may perform a multidirectional scan of a skin surface and perform an algorithmic analysis of collected data to determine presence of a skin condition, arranged in accordance with at least some embodiments of the present disclosure. FIG. 1 includes a scanning apparatus 100, a computing device 200, and network nodes 291 and 292. Scanning apparatus 100 may include one or more of a plurality of cameras 110 and/or a plurality of light sources 120, arranged at selected positions over a skin surface 105. Computing device 200 may comprise one or more of an image capture controller 274, image data store 226, transfer function processing 223, skin condition processing 224, skin condition library 227, comparison data store 228, and/or output devices 260. Network node 291 may also include a skin condition library 227. Network node 292 may be a medical service provider network node.

In FIG. 1, the cameras 110 and light sources 120 of the scanning apparatus 100 may be coupled to the computing device 200 and/or image capture controller 274 via wired or wireless connections 101. The image capture controller 274 may be adapted to communicate light source control signals 112 to the various light sources 120 via one or more connections 101, which are coupled between light sources 120 and the image capture controller 274. Image capture controller 274 may be adapted to communicate camera control signals 111 to the various cameras 110 via connections 101, which are coupled between the image capture controller 274 and the cameras 110. The image capture controller 274 may be configured to receive image data 231 from the various cameras 110 via connections 101.

The computing device 200 may also be coupled to the network nodes 291 and 291 via network connections 180. Skin condition identification data 235 may be sent from the computing device 200 to either of the network nodes 291 and 291, and skin condition identification data 235 may be received at the computing device 200 from either of the network nodes 291 and 291, as described further below.

The system illustrated in FIG. 1 may be configured to perform a multidirectional scan of a skin using the scanning apparatus 100, and also configured to perform an algorithmic skin health analysis using one or more processing modules such as 223 and 224. In some embodiments, the image capture controller 274 may be configured to perform a multidirectional scan by illuminating each of the light sources 120, one or more at a time, and to capture image data at one or more of the cameras 110, when one or more of the light sources 120 is illuminated. The captured image data 231 may be stored in the image data store 226.

Because skin surfaces such as 105 may not be completely opaque, but instead may be partially translucent, the image data 231 captured via the scanning apparatus 100 may comprise information (e.g., identified characteristics) about the skin surface 105 and/or the skin subsurface 106. In general, the computing device 200 may be configured to perform an algorithmic skin health analysis at least in part by analyzing the captured image data 231 to extract information about subsurface properties of the skin.

Transfer function processing 223 may be configured to operate on the captured image data 231 to calculate a subsurface transfer function 232 describing properties of the skin subsurface 106, as described in greater detail below. Skin condition processing 224 may be adapted to use the transfer function 232 (optionally along with additional data as described herein) to identify or determine one or more properties of the skin subsurface 106, and may also be adapted to correlate subsurface properties to skin conditions using the skin condition library 227. Skin condition processing 224 may be adapted to retrieve a skin condition 233 applicable to the determined properties of the skin subsurface 106 from the skin condition library 227, and may also be adapted to output the skin condition 233 to one or more output devices 260. For example, skin condition processing 224 may be configured to output the skin condition 233 to a display, where a technician or patient may be informed of the skin condition 233.

Figure 4:
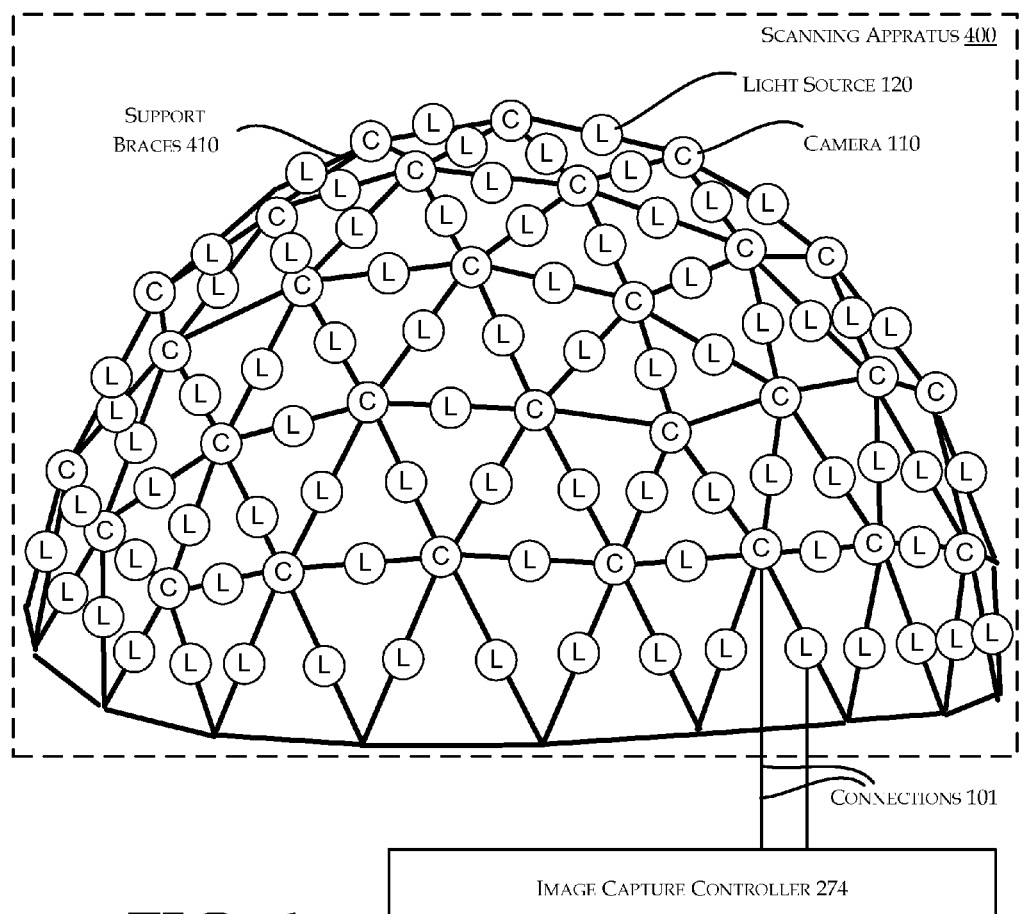
FIG. 4 is a diagram illustrating an example dome scanning apparatus.
Figure 5:
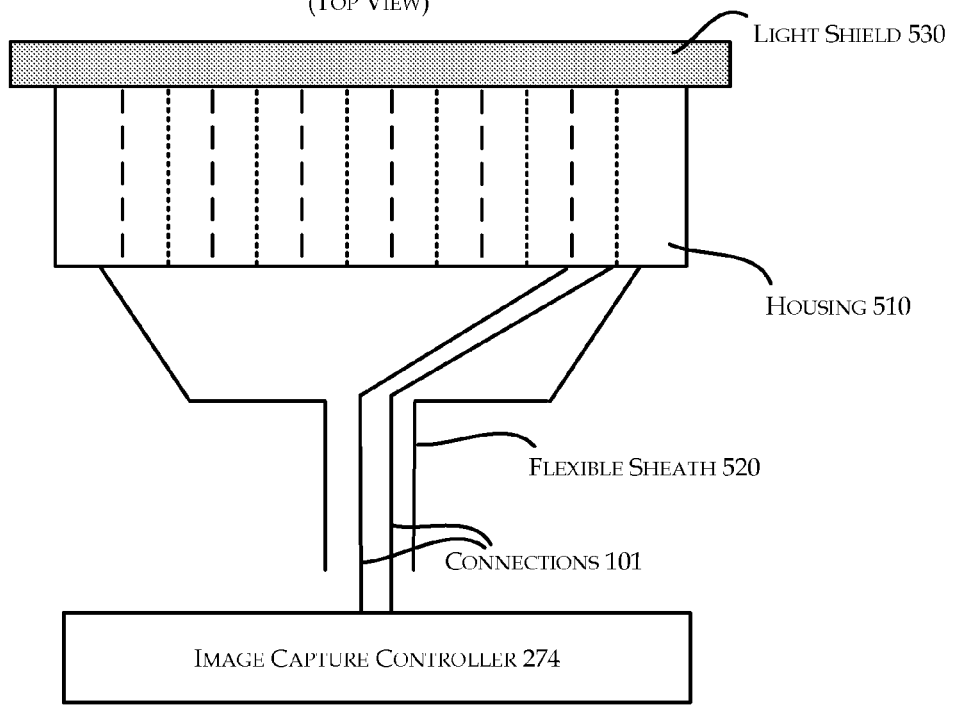
FIG. 5 is a diagram illustrating top and front views of an example handheld scanning apparatus.
Figure 5:
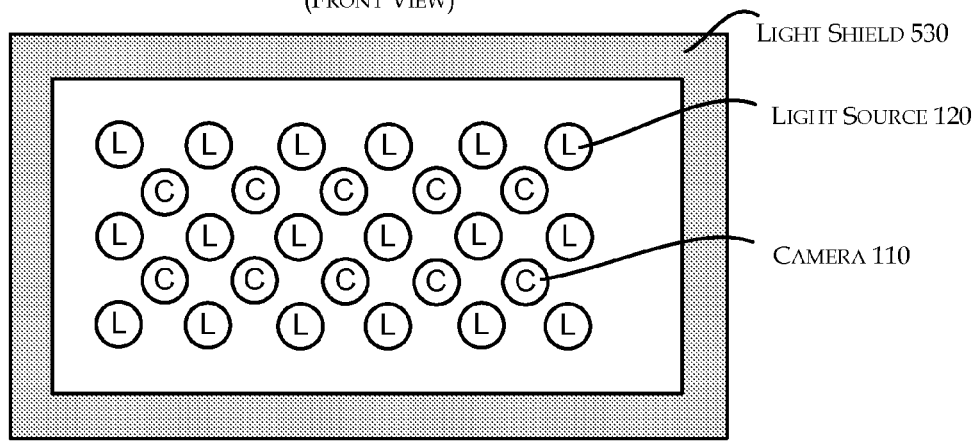

Various scanning apparatus 100 configurations may be applied in some embodiments. Example scanning apparatus 100 configurations are illustrated in FIG. 4 and FIG. 5. In addition to various physical arrangements of lights and cameras illustrated in FIG. 4 and FIG. 5, a scanning apparatus 100 may be configured to employ one or more light sources 120 emitting light frequencies that are selected as advantageous to the algorithmic skin health analysis described herein. Selected frequencies may be in the visible and/or in the nonvisible (infrared and ultraviolet) portion of the spectrum. Also, a single light source may be adapted to emit a range of different frequencies, for example, a traditional white light corresponds to a range of frequencies in the visible light spectrum. Light sources may be selected and/or filtered to select and/or optimize the frequencies emitted by the light source.

A scanning apparatus 100 may be configured with any of a variety of camera types. In general, the cameras 110 may be configured to produce digital images of a skin surface. High-definition digital cameras may be capable of capturing color images with a high degree of accuracy and detailed data for algorithmic skin health analysis. However, camera size and camera cost may provide constraints on the properties of cameras 110 selected for use with the system.

In some embodiments, the scanning apparatus 100 may be arranged to position light sources 120 and/or cameras 110 at roughly similar distances from a skin surface, and at regularly spaced angles with respect to a skin surface. Various distances and angles used in the scanning apparatus 100 may be accounted for when processing the image data 231, according to transfer function processing 223 embodiments provided herein. Light sources 120 and/or cameras 110 may be positioned at different positions as may be identified by coordinates along x, y and z axes, or as may be identified using any other coordinate system.

This disclosure is not limited to scanning apparatus 100 and/or image capture controller 274 configurations that illuminate a single light source at a time. In some embodiments, a plurality of light sources that are positioned close together may be illuminated as a group. In some embodiments, a plurality of light sources that are positioned even at widely different angles may be illuminated at substantially the same time. The positions of illuminated light sources may be accounted for by the computer 200 in conducting algorithmic analysis of the image data 231. In general, illuminated light sources positioned at widely different light source angles may yield more complex image processing in some circumstances, however such configurations are possible.

In some embodiments, the methods, devices, and/or systems related to detecting skin conditions described herein may be combined with any of the technologies described in U.S. patent application Ser. No. 12/714,060, filed Feb. 26, 2010, entitled "ECHOGRAM DETECTION OF SKIN CONDITIONS".

Each of the components illustrated in the computing device 200 and network nodes 291 and 292 may be configured to carry out one or more of the functions described below, in connection with FIG. 3.

Figure 2:
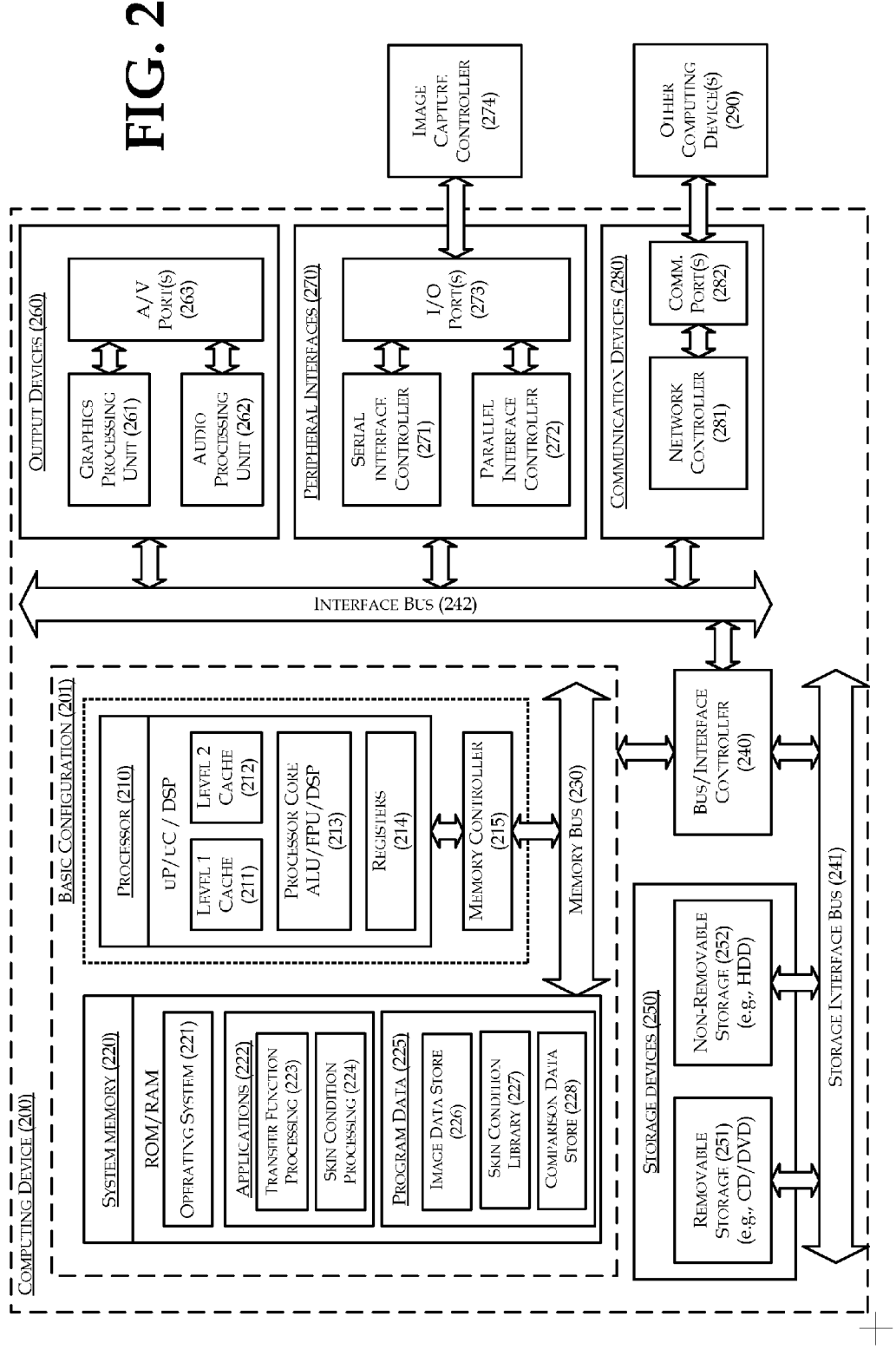
FIG. 2 is a block diagram illustrating a computing device as one example of the computing device illustrated in FIG. 1.

FIG. 2 is a block diagram illustrating a computing device as one example of the computing device illustrated in FIG. 1, arranged in accordance with at least some embodiments of the present disclosure. In a very basic configuration 201, computing device 200 may include one or more processors 210 and system memory 220. A memory bus 230 may be used for communicating between the processor 210 and the system memory 220.

Depending on the desired configuration, processor 210 may be of any type including but not limited to a microprocessor (μP), a microcontroller (μC), a digital signal processor (DSP), or any combination thereof. Processor 210 may include one or more levels of caching, such as a level one cache 211 and a level two cache 212, a processor core 213, and registers 214. The processor core 213 may include an arithmetic logic unit (ALU), a floating point unit (FPU), a digital signal processing core (DSP Core), or any combination thereof. A memory controller 215 may also be used with the processor 210, or in some implementations the memory controller 215 may be an internal part of the processor 210.

Depending on the desired configuration, the system memory 220 may be of any type including but not limited to volatile memory (such as RAM), non-volatile memory (such as ROM, flash memory, etc.), or any combination thereof. System memory 220 typically includes an operating system 221, one or more applications 222, and program data 225. Applications 223-224 may include, for example, transfer function processing module(s) 223 and skin condition processing module(s) 224. Program data 226-228 may include image data store 226, skin condition library 227, and comparison data store 228 that may be used by applications 223-224.

Computing device 200 may have additional features or functionality, and additional interfaces to facilitate communications between the basic configuration 201 and any required devices and interfaces. For example, a bus/interface controller 240 may be used to facilitate communications between the basic configuration 201 and one or more data storage devices 250 via a storage interface bus 241. The data storage devices 250 may be removable storage devices 251, non-removable storage devices 252, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives, to name a few. Example computer storage media may include volatile and nonvolatile, removable and non-removable media implemented in any method or technology for storage of information, such as computer readable instructions, data structures, program modules, or other data.

System memory 220, removable storage 251, and non-removable storage 252 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that may be used to store the desired information and that may be accessed by computing device 200. Any such computer storage media may be part of device 200.

Computing device 200 may also include an interface bus 242 for facilitating communication from various interface devices (e.g., output interfaces, peripheral interfaces, and communication interfaces) to the basic configuration 201 via the bus/interface controller 240. Example output devices 260 include a graphics processing unit 261 and an audio processing unit 262, which may be configured to communicate to various external devices such as a display or speakers via one or more A/V ports 263. Any such external devices may be used to communicate a detected skin condition 223 to a patient, technician, doctor, or other entity. Example peripheral interfaces 270 may include a serial interface controller 271 or a parallel interface controller 272, which may be configured to communicate through either wired or wireless connections with external devices such as an image capture controller 274, in embodiments in which an image capture controller 274 may be configured as a peripheral device, as well as input devices (e.g., keyboard, mouse, pen, voice input device, touch input device, etc.) or other peripheral devices (e.g., printer, scanner, etc.) via one or more I/O ports 273. Other conventional I/O devices may be connected as well such as a mouse, keyboard, and so forth. An example communications device 280 includes a network controller 281, which may be arranged to facilitate communications with one or more other computing devices 290, such as network nodes 291 and 292 (illustrated in FIG. 1) over a network communication via one or more communication ports 282.

The computer storage media may be one example of a communication media. Communication media may typically be embodied by computer readable instructions, data structures, program modules, or other data in a modulated data signal, such as a carrier wave or other transport mechanism, and include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR), and other wireless media.

Computing device 200 may be implemented as a one or more personal computers and/or laptop computers attached to image scanning apparatus for example at a doctor's office or in a retail location such as a shopping mall. Computing device 200 may also be implemented in or across any of a wide variety of computing devices, including for example small-form factor portable (or mobile) electronic devices such as a cell phones, personal data assistants (PDA), and personal media player devices, application-specific devices, and/or hybrid devices that include any of the above functions.

Figure 3:
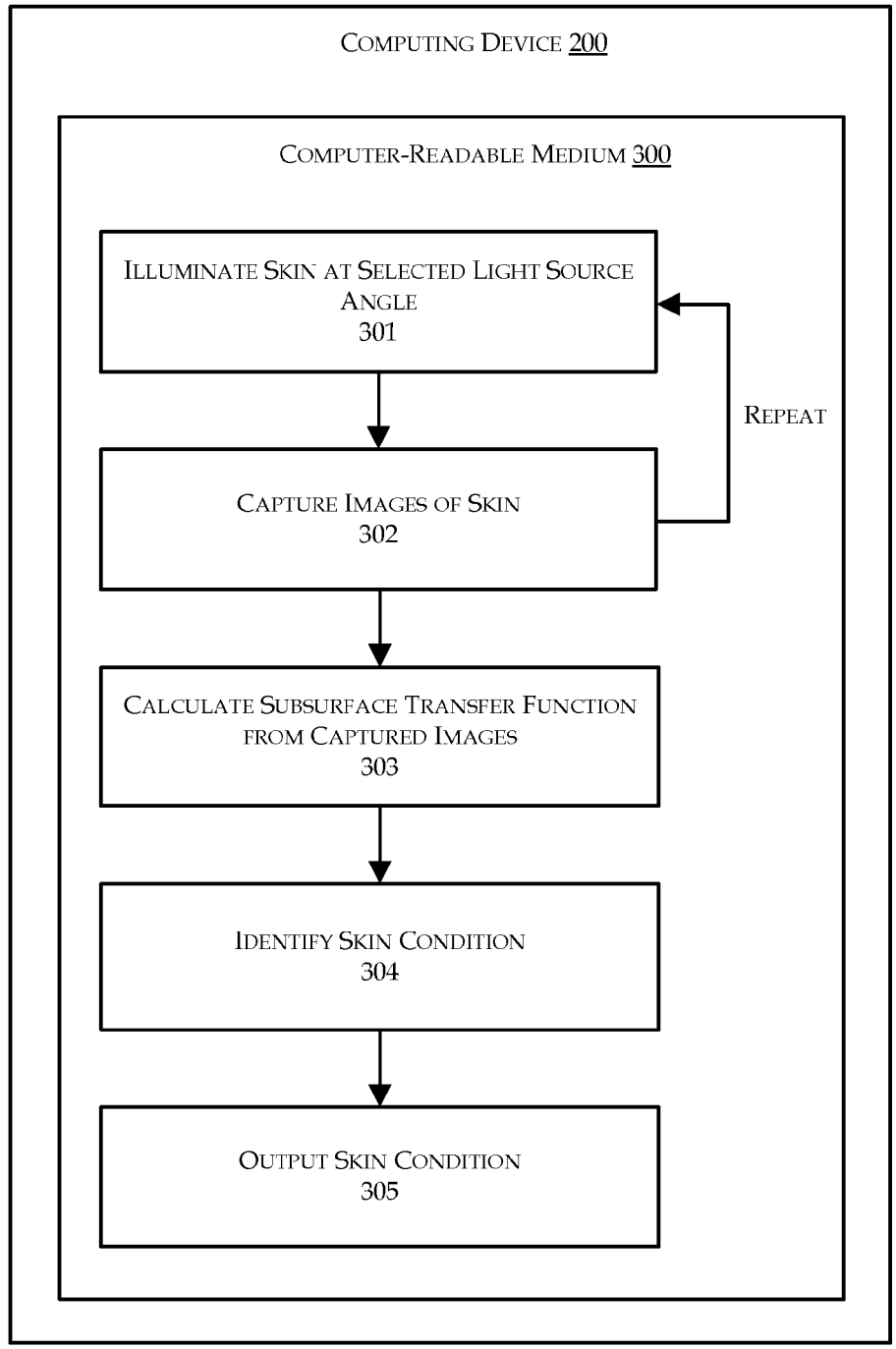
FIG. 3 is a flow diagram illustrating an example method that may collect images of a skin surface and perform an algorithmic analysis of collected data to determine presence of a skin condition.

FIG. 3 is a flow diagram illustrating an example method that may collect images of a skin surface and perform an algorithmic analysis of collected data to determine presence of a skin condition, arranged in accordance with at least some embodiments of the present disclosure. The example flow diagram may include one or more operations/modules, functions or actions as illustrated by blocks 301-305, which represent operations as may be performed in a method, functional modules in a computing device 200, and/or instructions as may be recorded on a computer readable medium 300. The illustrated blocks 301-305 may be arranged to provide functional operations including one or more of "Illuminate Skin Surface at Selected Light Source Angle" at block 301, "Capture Images of Skin Surface" at block 302, "Calculate Subsurface Transfer Function from Captured Images" at block 303, "Identify Skin Condition" at block 304, and/or "Output Skin Condition" at block 305.

In FIG. 3, blocks 301-305 are illustrated as being performed sequentially, with block 301 first and block 305 last. It will be appreciated however that these blocks may be reordered as convenient to suit particular embodiments, and that these blocks or portions thereof may be performed concurrently in some embodiments. It will also be appreciated that in some examples various blocks may be eliminated, divided into additional blocks, and/or combined with other blocks.

FIG. 3 illustrates an example method by which a multidirectional scan and algorithmic skin health analysis may be carried out using a system such as illustrated in FIG. 1. As a preliminary operation to performing the illustrated method, a subject (e.g. a person whose skin is to be analyzed) may first be positioned underneath the light sources and cameras of a scanning apparatus. Positioning the subject depends on the configuration of the scanning apparatus. For example, in embodiments utilizing a dome scanning apparatus such as FIG. 4, the subject may be seated inside the dome, and a tracking ball or other reference point may be affixed to the subject so that points on the subject's skin may be accurately compared across a plurality of images, even if the subject moves. In embodiments utilizing a handheld scanning apparatus such as FIG. 5, subject skin may be exposed for a technician to apply the handheld scanning apparatus over the skin to be analyzed.

At block 301, "Illuminate Skin at Selected Light Source Angle", an image capture controller 274 may be adapted to select one or more light sources from among the plurality of light sources 120 of a scanning apparatus 100, and apply one or more light source control signals 112 via connection(s) 101 to the one or more selected light sources 120, causing the selected light source to illuminate at an appropriate time interval when image data may be captured. As described above, each of the light sources 120 of a scanning apparatus 100 may be disposed at different light source angles with respect to the skin being illuminated. Therefore, selection and illumination of a light source of a scanning apparatus 100 described herein may inherently comprise illuminating a skin by a light source disposed at a selected light source angle with respect to the skin.

The image capture controller 274 may for example be adapted to select a first light source from a list of light sources of the scanning apparatus 100. In some embodiments, a multi-way light switch may be activated to select a light source. The light source control signal 112 may comprise a direct or alternating current power signal applied via a connection 101 and sufficient to illuminate the selected light source, or in the case of a "smart" light or "smart" scanning apparatus capable of receiving and processing instructions from the image capture controller 274, the light source control signal 112 may comprise an instruction to illuminate a selected light source. Block 301 may be followed by block 302.

At block 302, "Capture Images of Skin Surface", an image capture controller 274 may cause the cameras 110 of a scanning apparatus applicable to a scanning operation (in some embodiments, all of the cameras 110) to capture images of a skin illuminated by a selected light source. For example, immediately following an illumination of a light source according to block 301, and while the skin is illuminated by the light source, an image capture controller 274 may simultaneously send camera control signals 111 via all of the connections 101 coupled to the cameras 110, to cause the cameras 110 to capture a plurality of images of the skin from a plurality of camera angles with respect to the skin.

The image capture controller 274 may be configured to maintain selected light source(s) in an illuminated state during an operation according to block 302, for example by maintaining the power signal applied via the connection 101. After an operation according to block 302 is complete, image capture controller 274 may deactivate the selected light source(s), select subsequent light source(s), and illuminate the subsequent light source(s). Blocks 301 and 302 may be repeated for each light source in a scanning apparatus that is applicable to a scanning operation, e.g. in some embodiments, all of the light sources in a scanning apparatus. After each light source has been illuminated and block 302 has been performed for each light source, the image capture controller 274 may notify an application such as 223 or 224 that image capture is complete, thereby initiating algorithmic analysis of captured image data.

The cameras 110 may be configured to automatically send captured image data 231 to image capture controller 274 and/or to computing device 200 for storage in the image data store 226, in response to capturing images pursuant to the camera control signals 111. The image data 231 may be organized in the image data store 226 according to the light source 120 illuminating the skin for each image, as well as camera position for each image. This allows detailed analysis of the images using known angles of incident light (corresponding to a light source) and known angles of reflected/scattered light (corresponding to camera position). As indicated above in the description of block 301, blocks 301 and 302 may be repeated for each light source in a scanning apparatus.

When images are captured for all cameras and all light sources corresponding to a desired scanning operation, block 302 may be followed by block 303, thereby initiating algorithmic analysis of captured image data. Otherwise, processing may continue from block 302 to block 301 where the illumination/capture procedures may be repeated.

At block 303, "Calculate Subsurface Transfer Function from Captured Images", a subsurface transfer function calculation algorithm may be applied to calculate a subsurface transfer function 232 from the image data 231 in the image store 226 applicable to a skin scan performed by the scanning apparatus 100. The use of an algorithm for calculating a subsurface transfer function in connection with identifying a skin condition is referred to herein as an algorithmic identification of a skin condition corresponding to the one or more subsurface properties of the skin. The term "electronic identification" is also used herein to refer to calculation by a computer or other electronic device. In general, a transfer function 232 may be calculated using image properties corresponding to each of a plurality of points on the skin in each of the plurality of images for each of the light source angles applied by the scanning apparatus 100. For example, light reflecting or scattering off the skin at a particular point, as recorded in images corresponding to each of the camera angles and each of the illumination angles, may be used to determine subsurface skin properties such as color of subsurface layers or structures, thickness of subsurface layers or structures, texture of subsurface layers or structures, and density of subsurface layers or structures. Such information may be compared across a plurality of analyzed points to determine subsurface skin properties comprising color, thickness, texture, and density as well as shape and size properties of subsurface layers or structures. These various example subsurface properties may be described using a transfer function, using any of the approaches available in the art, referenced herein, or as may become known or available.

An example of a subsurface transfer function is the Bidirectional Surface Scattering Reflectance Distribution Function (BSSRDF). In general, BSSRDF (denoted S) relates an outgoing radiance, $L_o(x_o, \omega_o)$ at a point $x_o$ in direction $\omega_o$, to an incident flux, $\Phi_i(x_i, \omega_i)$ at a point $x_i$ from direction $\omega_i$, as follows:

$$dL_o(x_o,\omega_o)=S(x_i,\omega_i;x_o,\omega_o)d\Phi_i(x_i,\omega_i)$$

Given a BSSRDF, an outgoing radiance may be computed by integrating incident radiance over incoming directions and area, and vice versa. Furthermore, light propagation in a participating medium may be described by a radiative transport equation, referred to in computer graphics as a volume rendering equation. In a radiative transport equation, properties of a medium may be described by an absorption coefficient, a scattering coefficient, and a phase function.

In some embodiments, simplified approaches for calculating a BSSRDF may be used, for example by using diffusion approximations, scattering terms, and/or Bidirectional Reflectance Distribution (BRDF) approximations, as is generally understood in the field of computer graphics.

Any available BSSRDF or other transfer function calculation approach may be used to generate skin maps which highlight subsurface properties and distinguish bodily marks with subsurface damage from those which are primarily pigmentation. In some embodiments, one or more subsurface skin properties identified from BSSRDF skin maps, along with other features such as surface color and comparison data from previous scans, may be used to algorithmically identify skin conditions, as well as to produce output graphics highlighting the skin conditions. Block 303 may be followed by block 304.

At block 304, "Identify Skin Condition", the transfer function determined in block 303 and/or subsurface properties defined by the transfer function may be used to identify a skin condition corresponding to the one or more subsurface properties of the skin. In some embodiments, skin condition processing module(s) 224 may be configured to compare the one or more subsurface properties of the skin to an electronic library of subsurface skin properties and corresponding skin conditions. For example, a transfer function 232 describing one or more subsurface properties may be compared to transfer functions stored in a skin condition library 227. The library 227 may comprise a plurality of skin conditions corresponding to stored transfer functions, stored transfer function categories, and/or stored transfer function features. For example, the library 227 may comprise a plurality of melanoma type skin conditions as well as malignant nevi conditions, cosmetic conditions such as scars, acne, moles and freckles corresponding to stored transfer functions, stored transfer function categories, and/or stored transfer function features. The skin condition processing module(s) 224 may be adapted to retrieve any skin condition 233 corresponding to stored transfer functions in the library 227 that match the transfer function 223 corresponding to the skin subsurface 106.

In some embodiments, block 304 may be configured to identify skin condition 233 data in any of a variety of forms. For example, in some embodiments skin condition 233 data may comprise a medical risk associated with a skin condition. If a transfer function 232 is identified as an X % melanoma risk (where X is 0%-100%) the melanoma (or other condition) probability may be retrieved. Similarly, where a benign cosmetic blemish is identified, data identifying a skin condition as a cosmetic blemish and optionally suggesting or providing cosmetic removal options may be provided.

In some embodiments, block 304 may be configured to securely send a calculated transfer function 232 or other subsurface property description data to the medical service provider network node 292 via network connections 180 as skin condition ID data 235. A medical service provider may analyze the skin condition ID data 235, attempt to identify a corresponding skin condition 233, and send any skin condition data back to the computer 200 via network connections 180 as skin condition ID data 235.

In embodiments configured with a library 227 stored at a network node 291, block 304 may be configured to securely send a calculated transfer function 232 or other subsurface property description data to the network node 291 via network connections 180 as skin condition ID data 235. The skin condition ID data 235 may be secured for example by being encrypted prior to sending, and subsequently decrypted at the network node 291. The network node 291 may then compare the transfer function 232 to stored transfer functions in the library 227, and may securely send an identified skin condition 233 to the computing device 200 via network connections 180 as skin condition ID data 235. Embodiments storing a skin condition library 227 at a network node 291 may collect skin condition ID data 235 from a plurality of sources, for example, from many different doctor offices equipped with a system described herein. Collected skin condition ID data 235 may be compiled and used to improve the accuracy of the library 227 as well as any algorithms used in conjunction with the library 227. In various alternative embodiments, the computing device may retrieve the library 227 from the network node 291, e.g., to avoid sending the transfer function 232 to the network node, which may increase the privacy or perceived privacy of the methods described herein.

In some embodiments, block 304 may use additional data to facilitate skin condition identification. For example, skin condition processing module(s) 224 may be configured to retrieve image data 231 from the image data store 226 to investigate image properties corresponding to a skin surface 105 location disposed over a feature of interest in the skin subsurface 106 that may be identified in a calculated transfer function 232. The opposite operation may also be performed, that is, identifying surface properties of interest in the image data 231 corresponding to the skin surface 105, then determining whether subsurface properties are present underneath identified surface properties.

Similarly, a comparison data store 228 may comprise comparison data 234, comprising data from previous scans of a same skin, allowing comparisons across multiple scans to determine changes in the skin from scan to scan. A change in skin properties often indicates medical risk. Therefore, if for example a particular surface or subsurface feature expands or multiplies between scans, data identifying properties as expanding, multiplying, or otherwise changing may be used, either independently or in addition to the subsurface properties, to identify a skin condition 233. Surface properties of the image data 231 as well as comparison data 231 of interest may also be sent to nodes 291 and 292 as skin condition ID data 235, along with the subsurface transfer function 232 as described above.

With regard to the comparison data store 228, the disclosed method may be further configured to store a transfer function 232 and/or other data described herein as comparison data 234 in the comparison data store 228, for subsequent use in future skin condition identification operations. Comparison data 234 may also comprise image data 231 and optionally identification information comprising, for example, identifiers for the scanned subject (e.g. person's name), a location of the scanned skin surface (e.g. right shoulder blade), and/or date of the scan. Block 304 may be followed by block 305.

At block 305, "Output Skin Condition", a skin condition 233 may be output to an output device 260. In some embodiments, data comprising a written identification of the skin condition 233 may be output to a display that is coupled to the computer 200 as an output device 260. In some embodiments, the output may be a privacy-protected output such as a printout that may be provided directly to the scanned subject. The output may also take the form of an email or fax to a subject's email address or fax number, and/or a doctor's email address or fax number. In some embodiments, an audio recording may be provided for listening by the subject or a technician or other professional administering the scan. The skin condition 233 output may be accompanied by additional information such as information describing known aspects and properties of the skin condition, known treatment options, and contact information for dermatologists or other professionals available to treat the skin condition 233.

In some embodiments, block 305 may comprise displaying an image of the skin and highlighting the one or more subsurface properties of the skin on the displayed image. For example an image may comprise a graphics representation of the scanned skin, with a line drawn around the part of the skin having subsurface properties of interest. Cross-sectional views and colored highlighting of surface and subsurface properties may also be provided. In some embodiments, displayed images may comprise animation showing probable progression of the skin condition if left untreated and/or showing treatment procedures for how the skin condition may be removed or otherwise treated.

FIG. 4 is a diagram illustrating an example dome scanning apparatus 400, arranged in accordance with at least some embodiments of the present disclosure. Dome scanning apparatus 400 may comprise support braces 410, a plurality of light sources 120 (denoted L in FIG. 4), and a plurality of cameras 110 (denoted C in FIG. 4).

The dome scanning apparatus 400 may be coupled to an image capture controller 274 via connections 101, which may be configured to communicate one or more of light source control signals 112, camera control signals 111, and/or image data 231 between the image capture controller 274 and the dome scanning apparatus 400, as illustrated in FIG. 1. Two connections 101 are illustrated in FIG. 4 to represent connections 101 which may be used to couple all of the light sources 120 and cameras 110 to the image capture controller 274. The connections 101 may be separately wired parallel connections in some embodiments. In some embodiments, for example, where smart cameras 110 and/or light sources 120 are used which are addressable, the connections 101 may be implemented by a bus coupled to cameras 110 and/or light sources 120.

The dome scanning apparatus 400 provides an example of a scanning apparatus 100. In some embodiments, the dome scanning apparatus 400 may be arranged as an overhead dome. The dome scanning apparatus 400 may comprise, for example, a computer graphics scanning apparatus of a type similar to scanning apparatus for the movie-making industry. A subject may be positioned underneath the dome, where the subject may expose one or more skin surfaces to the lights 120 and cameras 110 of the dome. In some arrangements, a camera 110 may be positioned at one or more intersections of the support braces 410, and a light source 120 may be positioned along the body of one or more support braces. It will be appreciated that this arrangement involves lights and cameras at a plurality of different positions and angles with respect to the skin surface of a subject disposed in the dome. In some embodiments, the dome scanning apparatus 400 allows for scanning large and/or multiple skin surfaces in a single scan.

A scan done by a dome scanning apparatus 400 may be utilized by a system such as FIG. 1, for example, to identify on the order of a million points on a skin surface and characterize each point from images from 16 directions (corresponding to 16 cameras) for each of the light sources (e.g. 150 light sources). By rapidly sequencing the light sources and capturing images when the subject is illuminated, an entire scan may take several minutes. Mathematically, in some examples, each point may correspond to about 900-1200 data points which may be used to generate the subsurface transfer function characterizing the skin.

In some embodiments, the dome scanning apparatus 400 may comprise different configurations for support braces 410, and may comprise different numbers and positioning of light sources 120 and cameras 110, as will be appreciated. Sixteen (16) digital cameras and one hundred fifty (150) Light Emitting Diode (LED) light sources can be used in some special effects-type scanners, and a similar configuration may be used in the dome scanning apparatus 400 in some embodiments. Shapes other than domes may also be applied, for example, a flat structure disposed above a subject may be suitable for some embodiments. Camera, light source, and/or algorithmic processing configurations may be modified to accommodate camera and light source positioning according to different configurations of support braces 410.

In some embodiments, a tracking ball or other object may be affixed to a subject to accommodate for movement of the subject between images. Image processing may account for positioning of skin surfaces by referencing tracking ball position and orientation. In some embodiments, the function of a tracking ball may be accomplished by algorithmically determining relative positioning of a skin surface in each analyzed image. Image orientation analysis technologies may be applied for identifying an object, such as a skin surface, across a plurality of images, and determining camera distance and angle from the object in each of the images.

FIG. 5 is a diagram illustrating top and front views of an example handheld scanning apparatus 500, arranged in accordance with at least some embodiments of the present disclosure. The top view of the handheld scanning apparatus 500 comprises a light shield 530 affixed atop a housing 510, and a flexible sheath 520 affixed to the underside of the housing 510. The top view also illustrates an image capture controller 274.

A plurality of connections 101 are shown traversing the interior of the flexible sheath 520 and housing 510 from the image capture controller 274 to the top of the housing 510. Connections 101 may be bundled in the flexible sheath 520 and may spread out to couple to light sources 120 and cameras 110 illustrated in the front view of the handheld scanning apparatus 500. Connections 101 may be configured to communicate one or more of light source control signals 112, camera control signals 111, and/or image data 231 between the image capture controller 274 and the handheld scanning apparatus 500, as illustrated in FIG. 1. Two connections 101 are illustrated in FIG. 5 to represent connections 101 which may couple the light sources 120 and cameras 110 to the image capture controller 274. Connections 101 may for example comprise a bus implemented in conjunction with addressable cameras 110 and/or light sources 120, to allow for individual control of the cameras 110 and/or light sources 120.

The front view of the handheld scanning apparatus 500 comprises a rim of the light shield 530 surrounding a plurality of light sources 120 and a plurality of cameras 110. The light sources 120 and cameras 110 may be interspersed to allow for different light source and camera angles and positions when the front of the handheld scanning apparatus 500 is positioned over a skin surface.

The handheld scanning apparatus 500 provides an example of a scanning apparatus 100. In some embodiments, the handheld scanning apparatus 500 may be designed to be held over a skin surface to perform a scan of the skin surface, as described above. In some embodiments, light sources 120 and cameras 110 may comprise light source and camera elements disposed on the handheld scanning apparatus 500 as illustrated in the front view. In some embodiments, connections 101 may comprise fibers adapted to transmit light to and/or from light source and camera elements disposed elsewhere. Using fibers as part of light sources 120 and/or cameras 110 may reduce bulk of the handheld scanning apparatus 500 in some embodiments.

A light shield 530 may allow for contacting a skin surface with the handheld scanning apparatus 500. The light shield 530 may provide a known separation between the light sources 120 and cameras 110 and the skin surface, which in turn governs the positions and angles of the light sources 120 and cameras 110 for the purpose of subsequent algorithmic skin health analysis. The light shield 530 may furthermore block ambient light from reflecting off the skin at uncontrolled angles.

Figure 6:
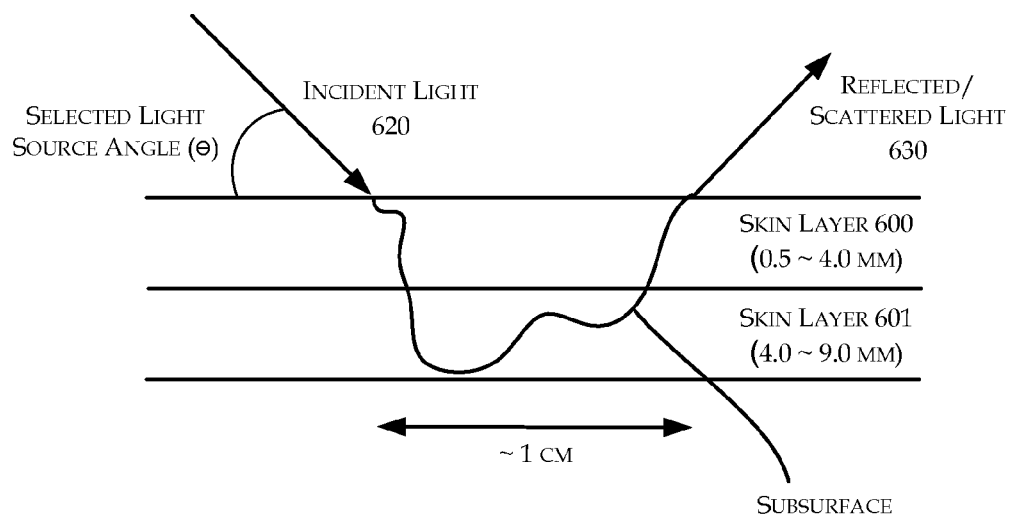
FIG. 6 is a diagram illustrating an example subsurface light path affected by subsurface properties of the skin; all arranged in accordance with at least some embodiments of the present disclosure.

FIG. 6 is a diagram illustrating an example subsurface light path affected by subsurface properties of the skin, in accordance with at least some embodiments of the present disclosure. FIG. 6 includes incident light 620 striking a skin at a selected light source angle $\theta$. The light travels a subsurface light path 603, through skin layer 600 and skin layer 601. Reflected/scattered light 630 corresponding to the incident light 620 travels away from the skin after following light path 603. Reflected/scattered light 630 may be detected by a camera positioned in the path of the reflected/scattered light 630, to produce an image that may be used to capture properties of the reflected/scattered light 630 and use such properties to determine subsurface properties of skin layers 600 and 601 as demonstrated herein. FIG. 6 comprises example scale indications of about 0.5 millimeters (mm) to about 4.0 mm depth of the layer 600, about 4.0 mm to about 9.0 mm depth of the layer 601, and around 1 cm length of the subsurface light path 603.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an"

should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain example techniques have been described and shown herein using various methods, devices and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

The invention claimed is:

1. A method for detecting skin conditions associated with a skin of a subject, the method comprising:
   activating a first light source to illuminate the skin, wherein the first light source is disposed at a first light source angle with respect to the skin;
   capturing a first plurality of images of the skin while the skin is illuminated by the first light source, from a first plurality of camera angles with respect to the skin;
   activating a second light source to illuminate the skin, wherein the second light source is disposed at a second light source angle with respect to the skin;
   capturing a second plurality of images of the skin while the skin is illuminated by the second light source, from a second plurality of camera angles with respect to the skin, wherein the first plurality of camera angles are at least partially different from the second plurality of camera angles;
   evaluating, by a computing device, image data from the first plurality of images and image data from the second plurality of images to identify properties corresponding to each of a plurality of points on the skin for each of the first and second light source angles to calculate a subsurface transfer function for the skin, wherein the subsurface transfer function describes one or more subsurface properties of the skin; and
   comparing, by a computing device, the subsurface transfer function to subsurface transfer functions in an electronic library of subsurface transfer functions and corresponding skin conditions to identify a skin condition for the subject, wherein the electronic library comprises one or more subsurface transfer functions corresponding to one or more melanoma skin conditions, and wherein the electronic library comprises one or more subsurface transfer functions corresponding to one or more other known skin conditions.

2. The method for detecting skin conditions of claim 1, wherein the subsurface transfer function comprises a bidirectional surface scattering reflectance distribution function.

3. The method for detecting skin conditions of claim 1, wherein comparing the subsurface transfer function to an electronic library of subsurface transfer functions and corresponding skin conditions comprises sending the subsurface transfer function to a network node configured to perform the comparing.

4. The method for detecting skin conditions of claim 1, wherein the electronic library of subsurface transfer functions and corresponding skin conditions comprises a medical risk associated with a skin condition.

5. The method for detecting skin conditions of claim 1, further comprising electronically communicating the subsurface transfer function to a medical service provider for further analysis.

6. The method for detecting skin conditions of claim 1, further comprising electronically comparing the subsurface transfer function to one or more subsurface transfer functions identified from images captured prior to the first plurality of images to determine a change in the one or more subsurface transfer functions.

7. The method for detecting skin conditions of claim 1, further comprising providing a display output comprising an identified skin condition.

8. A device configured to detect skin conditions associated with a skin of a subject, the device comprising:
   a processor; and
   a computer readable medium having computer-executable instructions stored thereon, the instructions configured to:
      activate a first light source to illuminate the skin, wherein the first light source is disposed at a first light source angle with respect to the skin;
      capture a first plurality of images of the skin while the skin is illuminated by the first light source, from a first plurality of camera angles with respect to the skin;
      activate a second light source to illuminate the skin, wherein the second light source is disposed at a second light source angle with respect to the skin;
      capture a second plurality of images of the skin while the skin is illuminated by the second light source, from a second plurality of camera angles with respect to the skin, wherein the first plurality of camera angles are at least partially different from the second plurality of camera angles;
      evaluate image data from the first plurality of images and image data from the second plurality of images to identify properties corresponding to each of a plurality of points on the skin for each of the first and second light source angles to calculate a subsurface transfer function for the skin, wherein the subsurface transfer function describes one or more subsurface properties of the skin; and compare the subsurface transfer function to subsurface transfer functions in an electronic library of subsurface transfer functions and corresponding skin conditions to identify a skin condition for the subject, wherein the electronic library comprises one or more subsurface transfer functions corresponding to one or more melanoma skin conditions, and wherein the electronic library comprises one or more subsurface transfer functions corresponding to one or more other known skin conditions.

9. The device configured to detect skin conditions of claim 8, wherein the subsurface transfer function comprises a bidirectional surface scattering reflectance distribution function.

10. The device configured to detect skin conditions of claim 8, wherein comparing the subsurface transfer function to an electronic library of subsurface transfer functions and corresponding skin conditions comprises sending the subsurface transfer function to a network node configured to perform the comparing.

11. The device configured to detect skin conditions of claim 8, wherein the electronic library of subsurface transfer functions and corresponding skin conditions further comprises a medical risk associated with a skin condition.

12. The device configured to detect skin conditions of claim 8, the computer readable medium further comprising instructions configured to electronically communicate the subsurface transfer function to a medical service provider.

13. The device configured to detect skin conditions of claim 8, the computer readable medium further comprising instructions configured to electronically compare the subsurface transfer function to one or more subsurface transfer functions identified from images captured prior to the first plurality of images to determine a change in the one or more subsurface transfer functions.

14. The device configured to detect skin conditions of claim 8, the computer readable medium further comprising instructions configured to provide a display output comprising an identified skin condition.

15. A non-transitory computer readable medium having computer-executable instructions stored thereon, the instructions configured to detect skin conditions associated with a skin of a subject, the instructions configured to:
   activate a first light source to illuminate the skin, wherein the first light source is disposed at a first light source angle with respect to the skin;
   capture a first plurality of images of the skin while the skin is illuminated by the first light source, from a first plurality of camera angles with respect to the skin;
   activate a second light source to illuminate the skin, wherein the second light source is disposed at a second light source angle with respect to the skin;
   capture a second plurality of images of the skin while the skin is illuminated by the second light source, from a second plurality of camera angles with respect to the skin, wherein the first plurality of camera angles are at least partially different from the second plurality of camera angles;
   evaluate image data from the first plurality of images and image data from the second plurality of images to identify properties corresponding to each of a plurality of points on the skin for each of the first and second light source angles to calculate a subsurface transfer function for the skin, wherein the subsurface transfer function describes one or more subsurface properties of the skin; and compare the subsurface transfer function to subsurface transfer functions in an electronic library of subsurface transfer functions and corresponding skin conditions to identify a skin condition for the subject, wherein the electronic library comprises one or more subsurface transfer functions corresponding to one or more melanoma skin conditions, and wherein the electronic library comprises one or more subsurface transfer functions corresponding to one or more other known skin conditions.

16. The computer readable medium of claim 15, wherein the subsurface transfer function comprises a bidirectional surface scattering reflectance distribution function.

17. The computer readable medium of claim 15, wherein comparing the subsurface transfer function to an electronic library of subsurface transfer functions and corresponding skin conditions comprises sending the subsurface transfer function to a network node configured to perform the comparing.

18. The computer readable medium of claim 15, wherein the electronic library of subsurface transfer functions and corresponding skin conditions further comprises a medical risk associated with a skin condition.

19. The computer readable medium of claim 15, further comprising instructions configured to electronically communicate the subsurface transfer function to a medical service provider for further analysis.

20. The computer readable medium of claim 15, further comprising instructions configured to electronically compare the subsurface transfer function to one or more subsurface transfer functions identified from images captured prior to the first plurality of images to determine a change in the one or more subsurface transfer functions.

21. The computer readable medium of claim 15, further comprising instructions configured to provide a display output comprising an identified skin condition.

22. The method for detecting skin conditions of claim 1, further comprising affixing a reference point to the subject to track points on the skin for each of the first and second light source angles as the subject moves.

23. The method for detecting skin conditions of claim 1, further comprising holding a handheld scanning apparatus over the skin to capture the first and second plurality of images of the skin.

24. The method for detecting skin conditions of claim 1, further comprising positioning the subject in a dome scanning apparatus to capture the first and second plurality of images of the skin.

25. The method for detecting skin conditions of claim 1, further comprising storing the first and second plurality of images of the skin in an image data store according to light source and camera position for each image.

26. The method for detecting skin conditions of claim 7, wherein the display output comprises one or more of:
   highlighting at one or more subsurface properties of the skin;
   a cross-sectional view of one or more subsurface properties of the skin;
   an animation showing progression of the identified skin condition for the subject if left untreated; or
   an animation showing a treatment procedure for the identified skin condition.

* * * * *

UNITED STATES PATENT AND TRADEMARK OFFICE
CERTIFICATE OF CORRECTION

| | |
|---|---|
| PATENT NO. | : 8,855,751 B2 |
| APPLICATION NO. | : 12/714011 |
| DATED | : October 7, 2014 |
| INVENTOR(S) | : Kruglick |

It is certified that error appears in the above-identified patent and that said Letters Patent is hereby corrected as shown below:

On the Title Page, in item (56), under "OTHER PUBLICATIONS", in Column 2, Lines 2-5, delete "Curiel-Lewandrowski, C., et al., "Use of In Vivo Confocal Microscopy in Malignant Melanoma an Aid in Diagnosis and Assessment of Surgical and Nonsurgical Therapeutic Approaches," Am Med Assoc, vol. 140, Issue 9, pp. 1127-1132.".

On the Title Page, in item (56), under "OTHER PUBLICATIONS", in Column 2, Lines 10-11, delete "D'Eon, Advanced Techniques for Realistic Real-Time Skin Rendering; Chapter 14 from book GPU Gems 3; 58 pages.".

On the Title Page, in item (56), under "OTHER PUBLICATIONS", in Column 2, Lines 12-14, delete "Tsumura, Image-based skin color and texture analysis/synthesis by extracting hemoglobin and melanin information in the skin; Article; 10 pages.".

On Title Page 2, in item (56), under "OTHER PUBLICATIONS", in Column 2, Lines 1-4, delete "Gonzàlez, S, and Gilaberte-Calzada‡, Y., "In vivo reflectance-mode confocal microscopy in clinical dermatology and cosmetology," International Journal of Cosmetic Science, vol. 30, No. 1 (2008): 1-17.".

On Title Page 2, in item (56), under "OTHER PUBLICATIONS", in Column 2, Lines 25-28, delete "Rochester., "New Studies Show Effectiveness of Reflective Confocal Microscopy," accessed at http://www.prlog.org/10026545-new-studies-show-effectiveness-of-reflective-confocal-microscopy.html, Aug. 7, 2007, pp. 2.".

On Title Page 2, in item (56), under "OTHER PUBLICATIONS", in Column 2, Line 36, delete "asseessment" and insert -- assessment --, therefor.

On Title Page 2, in item (56), under "OTHER PUBLICATIONS", in Column 2, Line 51, delete "12/714,060;" and insert -- 12/714,011; --, therefor.

Signed and Sealed this
Twelfth Day of May, 2015

Michelle K. Lee
*Director of the United States Patent and Trademark Office*

CERTIFICATE OF CORRECTION (continued)
U.S. Pat. No. 8,855,751 B2

In the Drawings

In Fig. 2, Sheet 2 of 6, delete "uP/uC/DSP" and insert -- µP/µC/DSP --, therefor.

In the Specification

In Column 5, Lines 54-55, delete "communications" and insert -- communication --, therefor.

In Column 8, Line 50, delete "(BRDF)" and insert -- function (BRDF) --, therefor.

In Column 10, Line 17, delete "data 231" and insert -- data 234 --, therefor.

In Column 13, Line 47, delete "and or" and insert -- and/or --, therefor.